US012773796B2

(12) United States Patent
Vogele

(10) Patent No.: US 12,773,796 B2
(45) Date of Patent: Oct. 27, 2026

(54) POSITIONING ARM

(71) Applicant: iSYS Medizintechnik GmbH, Kitzbühel (AT)

(72) Inventor: Michael Vogele, Schwabmünchen (DE)

(73) Assignee: Isys Medizintechnik GmbH, Kitzbühel (AT)

( * ) Notice: Subject to any disclaimer, the term of this patent is extended or adjusted under 35 U.S.C. 154(b) by 533 days.

(21) Appl. No.: 18/269,898

(22) PCT Filed: Dec. 22, 2021

(86) PCT No.: PCT/EP2021/087291
§ 371 (c)(1),
(2) Date: Jun. 27, 2023

(87) PCT Pub. No.: WO2022/144273
PCT Pub. Date: Jul. 7, 2022

(65) Prior Publication Data
US 2024/0058973 A1 Feb. 22, 2024

(30) Foreign Application Priority Data
Dec. 29, 2020 (DE) ......................... 202020107591.8

(51) Int. Cl.
*B25J 18/00* (2006.01)
*A61B 90/00* (2016.01)

(52) U.S. Cl.
CPC ............. *B25J 18/002* (2013.01); *A61B 90/08* (2016.02)

(58) Field of Classification Search
CPC ........ B25J 18/002; A61B 90/08; A61B 34/30; A61B 2017/00477; A61B 2090/508; A61B 2090/571; A61B 90/50
(Continued)

(56) References Cited

U.S. PATENT DOCUMENTS 2,561,196 A * 7/1951 Gauthier ................ B23K 3/087 269/254 R
4,461,284 A * 7/1984 Fackler .................. A61B 90/50 403/56
(Continued)

FOREIGN PATENT DOCUMENTS

CN 108327306 A * 7/2018 ............. B65H 35/06
EP 2085186 A2 8/2009
(Continued)

OTHER PUBLICATIONS

Helmut Kapczynski: "Surgical Instruments 101 An Introduction to KMedic Certified Instruments", Internet Citation, Jan. 1, 1997 (Jan. 1, 1997), Seiten 1-181, XP008172530, Gefunden im Internet: URL:http://www.teleflex.com/en/usa/pdf/ KMedic_Surgical_ Instruments_101.pdf [gefunden am Oct. 3, 2014]. 181 pgs.
(Continued)

*Primary Examiner* — Kimberly T Wood
(74) *Attorney, Agent, or Firm* — Lerner David LLP

(57) ABSTRACT

A positioning arm for positioning instruments, devices or tools, is disclosed. The positioning arm includes at least two arm elements pivotably connected to one another about a pivot axis via a central joint. At least one of the arm elements includes a further joint at an end opposite the central joint. The positioning arm includes a blocking device for blocking and releasing the central joint and the at least one further joint. The blocking device is arranged on the central joint and effects the blocking and release of the further joints via at least one transmission device formed on the arm elements. The transmission device is formed by a pair of gripper arms which also form the arm elements.

20 Claims, 11 Drawing Sheets

(58) Field of Classification Search
USPC ... 248/276.1, 288.31, 292.12, 292.13, 274.1, 248/279.1, 281.11
See application file for complete search history.

(56) References Cited

U.S. PATENT DOCUMENTS

| | | | | |
|---|---|---|---|---|
| 5,984,864 | A | 11/1999 | Fox et al. | |
| 7,090,181 | B2 * | 8/2006 | Biba | F16M 11/2078 403/56 |
| 7,207,992 | B2 * | 4/2007 | Ritland | A61B 17/7007 606/86 A |
| 7,294,140 | B2 | 11/2007 | Mosnier et al. | |
| 7,523,904 | B2 * | 4/2009 | Carnevali | F16M 13/02 248/176.1 |
| 8,192,467 | B2 * | 6/2012 | Felix | A61B 17/7052 606/250 |
| 10,687,915 | B2 | 6/2020 | Schlosser et al. | |
| 2004/0089777 | A1 * | 5/2004 | Schilt | A61B 90/50 248/292.12 |
| 2008/0045972 | A1 * | 2/2008 | Wagner | A61B 90/39 606/130 |
| 2008/0230667 | A1 * | 9/2008 | Chapman | G01N 21/8806 248/122.1 |
| 2009/0178520 | A1 * | 7/2009 | Engelfried | B25F 5/026 81/489 |
| 2020/0085530 | A1 * | 3/2020 | Sauer, Md | A61B 1/00149 |
| 2020/0163658 | A1 * | 5/2020 | Krinninger | H01R 33/765 |
| 2022/0194748 | A1 * | 6/2022 | Homewood | B66C 1/442 |

FOREIGN PATENT DOCUMENTS

| | | | | |
|---|---|---|---|---|
| ES | 2277375 | T3 | 7/2007 | |
| JP | S59115303 | U * | 8/1984 | |
| JP | S59161028 | U | 10/1984 | |
| JP | 2013111220 | A | 6/2013 | |
| JP | 2018509273 | A | 4/2018 | |
| JP | 2020516331 | A | 6/2020 | |
| JP | 2020519327 | A | 7/2020 | |
| KR | 101582102 | B1 * | 1/2016 | B66C 1/28 |
| WO | WO 2017/144172 | A1 | 8/2017 | |

OTHER PUBLICATIONS

WO 2017/144172 A1 Machine Language Translation into English.

* cited by examiner

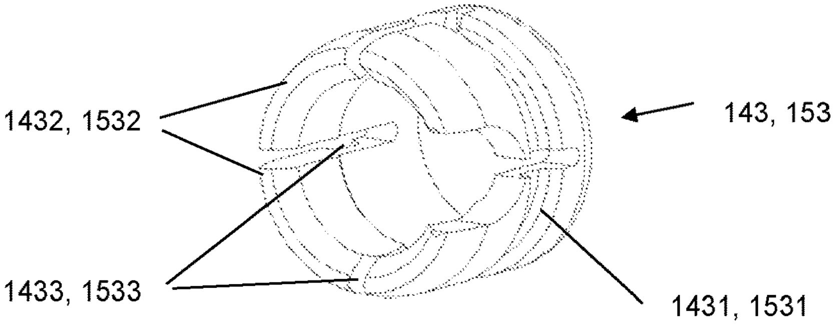
FIG. 14
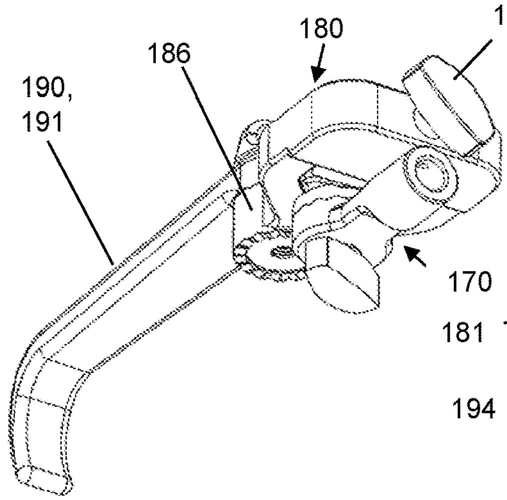
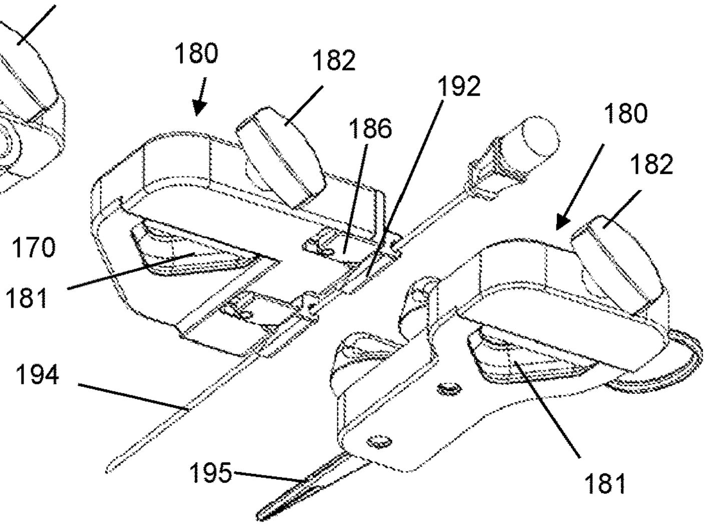
FIG. 15 FIG. 16 FIG. 17
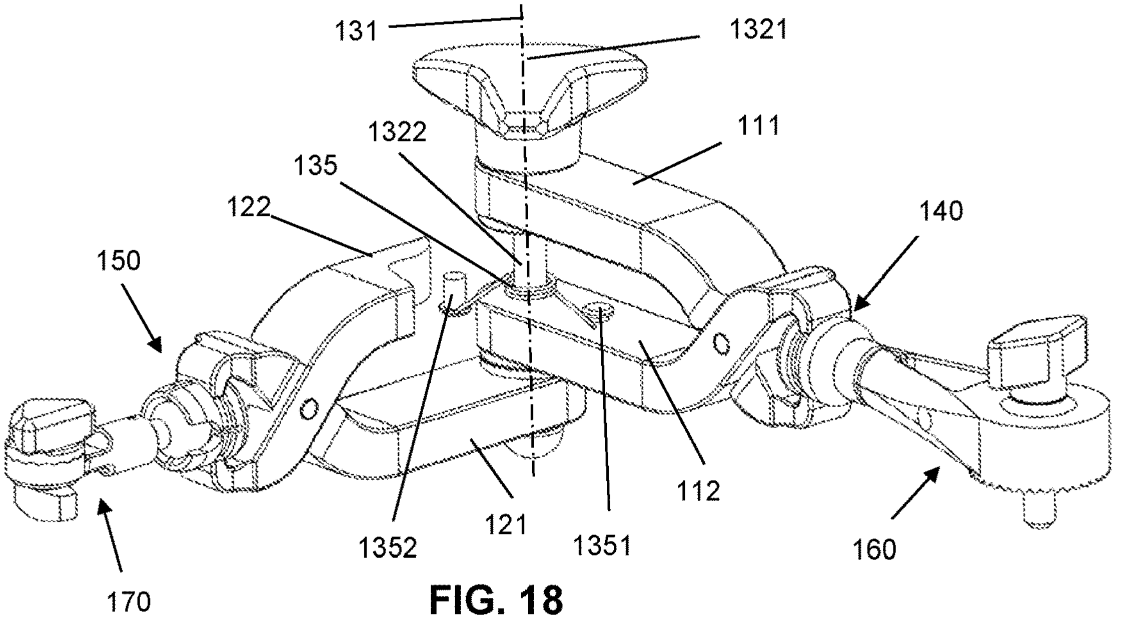
FIG. 18

POSITIONING ARM

CROSS REFERENCE TO RELATED APPLICATIONS

This application is a national phase application of International Application No. PCT/EP2021/087291, filed Dec. 22, 2021, which claims priority to German Patent Application 202020107591.8, filed on Dec. 29, 2020, the content of all of the aforementioned of which is herein incorporated by reference.

BACKGROUND OF THE INVENTION

Field of the Invention

The present invention relates to a positioning arm for positioning instruments, in particular medical instruments. However, the positioning arm according to the invention also allows a variety of other instruments, devices or tools to be precisely positioned. These may include, for example, measuring instruments, monitors, microphones, loudspeakers and lighting fixtures. Such positioning arms are also ideally suited for holding vessels and equipment in laboratories.

Description of Related Art

A wide variety of positioning arms with different requirements are known from the state of the art for different applications. Particularly in the case of positioning arms for positioning medical instruments, for example, very high demands are placed on the stability, reliability and operability of the positioning arms. Thus, numerous attempts have been made in the prior art to further develop and improve positioning systems taking these requirements into account.

For example, a positioning arm with a rotating body or swivel joint and two arm elements hinged thereto is known from the applicant's publication WO 2017/144 172 A1. In this case, the angle between the two arm elements is configured to be fixed by a ratchet attached to the rotary body via a coupling, a switch being provided on the coupling which locks the angular position of the arms relative to one another in a desired switch position.

The positioning arm known from WO 2017/144 172 A1 presents the advantage that, thanks to the ratchet, it is possible to easily lock, i.e. block the rotary joint of the positioning arm with relatively little force. In particular, it is also possible to operate the ratchet easily in a sterile environment, for example under a sterile covering foil. In addition, the ratchet allows a certain minimum torque to be specified so that the positioning arm is locked reliably.

However, the positioning arm known from WO 2017/144 172 A1 presents the disadvantage that operation is still dependent on the skill of a user. Therefore, a residual risk remains during usage if the user does not operate the ratchet correctly and the arm becomes misaligned during a surgical procedure. In addition, the ergonomics or usability are still not optimal. For example, when positioning the positioning arm, the user must simultaneously hold the instrument at the end of the positioning arm and keep an eye on the surgical field. Such a simultaneous procedure is very difficult for the user, especially since relatively high forces must be applied when locking the arm and the rotational movement when turning the ratchet can run counter to movements of the other hand. Since the positioning arm has to be repositioned many times before, during and after a surgical procedure, i.e. multiple opening and closing are required, a faster operating option would also be desirable.

Another positioning arm is known from the U.S. Pat. No. 10,687,915 B2. In this, pressure for locking joints is transmitted to the joints via hydraulically, pneumatically or mechanically adjustable pistons and/or linkages. This requires high closing forces and relatively complex transmission elements.

The well-known three-joint support arms or three-joint stands consist of a large number of components that are often very delicate and have to withstand very high compression and bending forces. This makes production expensive and one is very limited in the choice of materials. Hard metal alloys or special hardened steels must be used, especially for the pressure elements/pressure rods and in the joints (sometimes with special coatings) because other materials cannot withstand them. The use of lightweight aluminum or plastic materials (for better handling or for use in the X-ray beam or magnetic field of an MRI scanner) is therefore always accompanied by loss of the locking pressure in the joints and loss of the holding force of the arm in the case of the familiar three-joint holding arms or three-joint stands, and durability is also reduced.

Based on the aforementioned prior art, it is the object of the present invention to provide a positioning arm that eliminates the problems and disadvantages of the systems known from the prior art and has corresponding advantages over them. In particular, it is the object of the present invention to provide a positioning arm which permits ergonomically advantageous, convenient and rapid operation of the positioning arm.

BRIEF SUMMARY OF THE INVENTION

The solution according to the invention provides a positioning arm for positioning instruments or tools, which comprises at least two arm elements which are connected to one another by means of a central joint so as to be pivotable about a pivot axis. Thereby, at least one of the arm elements comprises a further joint at an end opposite to the central joint. The positioning arm further comprises a blocking device for blocking and releasing the central joint and the at least one further joint, which is arranged at the central joint and effects the blocking and release of the further joints via at least one transmission device formed on or by the arm elements. Due to the arrangement of the blocking device at the central joint, the actuation takes place in an ergonomically favorable grip area laterally above the patient.

The particularly simply constructed, robust positioning arm according to the invention is characterized by the fact that the transmission device is formed by at least one pair of pincer arms and, particularly preferably, by two pairs of pincer arms. The pincer arms each comprise a longer lever arm and a shorter gripping arm, the lever arms being connectable with their rear ends aligned in the region of the central joint by means of the blocking device and the gripping arms forming part of the further joints. This embodiment requires very low actuating forces because, in addition to the closing force of the blocking device, the pincer arms provide an additional lever transmission between the force application point at the ends of the longer lever arms and the force transmission point at the shorter gripping arms.

The embodiment according to the invention creates an articulated arm with three main joints which, unlike the known articulated arms, does not work with filigree pressure elements inside the arm elements requiring additional guides, but with robust pairs of pincers directly forming the arm elements.

Preferably, both arm elements each comprise a further joint and the blocking device is connected to the further joint by means of a transmission device in each case.

The positioning arm is used in particular to position or hold medical instruments, tools or aids reliably, i.e. safely and precisely, during an operation on a patient. Such reliable positioning of instruments or tools, for example needles, hooks, tweezers or markers, is essential, particularly during neurosurgical or bioptic procedures.

When using the positioning arm for positioning medical instruments, for example, one of the arm elements is configured to be connected via a further joint to a fastening device for an operating table. The other arm element can be designed to be connected accordingly via a further joint to an instrument holder designed particularly advantageously as a universal adapter. Instead of a fastening device for an operating table, an outer end of one of the arm elements can also be provided with a magnetic clamping device for fastening to a metallic surface or with a screw-on flange plate for temporary or permanent fastening to a wall or a carrier.

According to a first preferred embodiment, the at least one further joint comprises a rotatable clamping body. The rotatable clamping body is designed either as a ball or as a rotating sleeve, the latter being particularly advantageous for the additional mounting of a rotatable ball and thus permitting not only any desired rotation but also virtually any desired pivoting angle.

The simple robust design consisting of a few parts, of which at least two pincer arms in each case can be manufactured inexpensively as identical parts, and the ease of assembly also enable safe and efficient sterilization of all parts of the positioning arm, whereas known positioning arms comprise a large number of parts with numerous undercuts, bores, blind holes, adhesions or the like and are therefore difficult to dismantle for a sterilization process and difficult to access in all areas.

In addition to being simple to manufacture and easy to assemble, positioning arms according to the invention are also characterized by the fact that they are configured to fix even high payloads very securely and with millimeter precision while being lightweight. Since the pincer arms used are also very easy to manufacture from plastic, the positioning arms they form are usable directly, for example, in MRI applications in the radiation area of the tube.

The blocking device preferably comprises an actuating element displaceable in the axial direction of the central joint and connected to an actuating device. In a simpler embodiment, the actuating device can be formed by a rotary handle connected to a thread, by a clamping handle connected to an eccentric, or by a preferably battery-powered electric motor. Although blocking by means of the blocking device is preferably performed electrically, manual blocking or release of the joints may alternatively be possible. For example, the blocking device can be operated without electrical power via a thread or an eccentric. In connection with a design of the transmission device by pincer arms, an additional mechanical transmission takes place between force introduction and force transmission, which can lie approximately within a ratio of 1:2 to 1:10. Due to this additional transmission ratio, only relatively low actuation is required at the blocking device. The electrical energy required to operate the blocking device in the case of a motor drive is preferably supplied by means of an accumulator. This eliminates the need for cabling, which can be a source of danger inside the operating room.

The positioning arm according to the invention solves the task in an excellent way. Both with a manual actuating device and with a motorized actuating device, the blocking device can be operated very conveniently, easily and quickly. Moreover, the operation is designed to be at least substantially independent of the available forces of a user. Due to the additional transmission by means of the transmission device, the positioning arm can always be locked in a stable enough position even with a small amount of force and cannot be misaligned during operation. Furthermore, the small operating travels of the blocking device enable very fast operation. Complete locking of the joints of the positioning arm can be achieved within a few seconds.

Another advantage of the purely mechanically or electrically operated blocking device is its compactness. There have been enormous technical developments in electric drives in recent years. Alternative known pressure systems that work with compressed air, hydraulic oil or the like (see, for example, the U.S. Pat. No. 10,687,915 B2 mentioned at the beginning) are cost-intensive to manufacture, complex to use and maintain, and, because of the fluids used, pose a risk to the sterile surgical field and the user that can be avoided by the invention. Particularly with regard to sterility, it is advantageous that electric drives i.e. motors including the associated electronics are now also available in a way that can be sterilized, in particular autoclaved. This is particularly relevant for applications where it is not possible to work with a sterile covering foil. With regard to sterilizability, the entire positioning arm according to the invention is characterized by the fact that its few parts can be completely disassembled very easily and quickly for cleaning and can also be easily reassembled after sterilization.

In particular, the progressive opening of the individual joints may be desirable to prevent there being only one fully opened state in which all the joints of the positioning arm move back and forth in an unstable manner. By appropriately coordinating and adjusting the actuation paths of the blocking device, the transmission devices and the clamping bodies used in the other joints, it is possible to determine in a simple manner exactly which of the joints is the first to be fully locked at the beginning of the actuation of the blocking device and which is the last to be fully locked. By using clamping bodies with slightly different diameters or by using spacer washers in the area of the central joint, this sequence can also be changed subsequently if required.

The further joint preferably comprises a rotatable clamping body. A first advantageous embodiment provides that the further joint with a ball as clamping body is designed as a ball joint. A ball joint is a joint with a freely rotatable and pivotable ball. The transmission devices formed by the present pincer arms is configured to, for example, receive a ball directly between their gripping arms, which are preferably formed on the inside of their ends with slightly concave depressions in the manner of troughs, and lock it in place when the lever arms are pressed together.

According to a further advantageous embodiment, the further joint comprises a rotating sleeve which is rotatably held on the gripping arms of the pincer arms, for example by means of a groove or screw-in, and which is locked when the gripping arms are closed. Particularly advantageously, a slotted receptacle consisting of several segments is provided in a rotating sleeve at an end remote from the gripping arms for a ball of a ball joint, so that when the gripping arms are not locked, a rotation of the rotating sleeve and additionally a pivoting movement of the ball in the rotating sleeve provide additional degrees of freedom. When the gripping arms are locked, rotation of the rotating sleeve is simultaneously prevented and the ball is also firmly locked by pressing the segments of the rotating sleeve together.

Another advantageous embodiment provides that the clamping body is connected by means of a tie rod to a connecting joint (113; 123) connecting two pincer arms. In this case, the tie rod pulls the clamping body against a trough-shaped seat at the end of the pincer arms when they are locked.

According to an advantageous further development of the invention, an electric blocking device comprises an electric motor with an output shaft aligned perpendicular to the axis of the central joint and connected to the blocking device by means of a bevel gear drive or worm gear. With such a design, the advantage lies in a particularly high degree of compactness. The electrical blocking device can be arranged on one of the arm elements to save space. Usually, in most applications, only very limited space is available and the best possible access from the surgeon to the operating field is of high relevance. Such a motor-gearbox arrangement, which can also be used for the present invention, is already described in the applicant's earlier application DE 10 2020 122 352.8 of 26 Aug. 2020, which was also filed as PCT/EP2021/067028 on 22 Jun. 2021 and the contents of which are to that extent also made part of the disclosure content of this application.

All of the advantages described above can be used particularly well in a positioning arm for positioning medical instruments. Instead of simple medical devices and instruments, the positioning arm can also be used to position miniaturized robots in a position close to the area of application, in which case the further actuation of at least one instrument—such as a puncture needle—is preferably performed remotely by means of a robot that can be moved with several degrees of freedom.

BRIEF DESCRIPTION OF THE SEVERAL VIEWS OF THE DRAWINGS

Further features, advantages and embodiments of the invention will be apparent from the following description based on the figures, wherein:

FIG. 14 depicts an enlarged view of a rotating sleeve as shown in FIG. 1, FIG. 15-17 depicts different holders for different instruments or tools can be coupled with a universal adapter engaged in FIG. 15, FIG. 18 depicts a variant of FIG. 1 with a spring element arranged in the region of the central joint and resiliently preloading the arm elements, the spring element being designed as an exemplary torsion bar spring, one of the pincer arms in the region of the central joint having been removed to illustrate this.

DETAILED DESCRIPTION OF THE INVENTION

Figure 1:
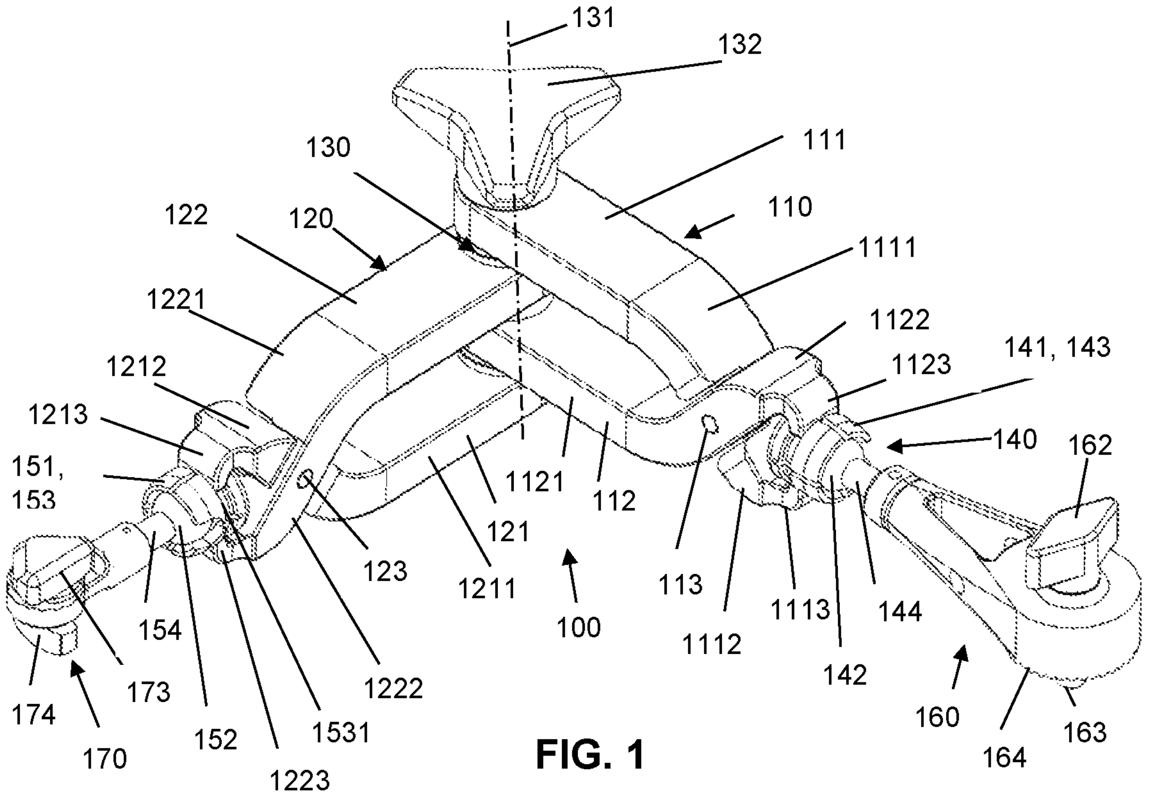
FIG. 1 depicts a perspective view of a positioning arm according to the invention with two arm elements connected in a central joint, each formed by a pair of pincer arms, and each comprising a further externally located joint, the clamping bodies of the externally located joints being formed by rotating sleeves and balls received therein.
Figure 2:
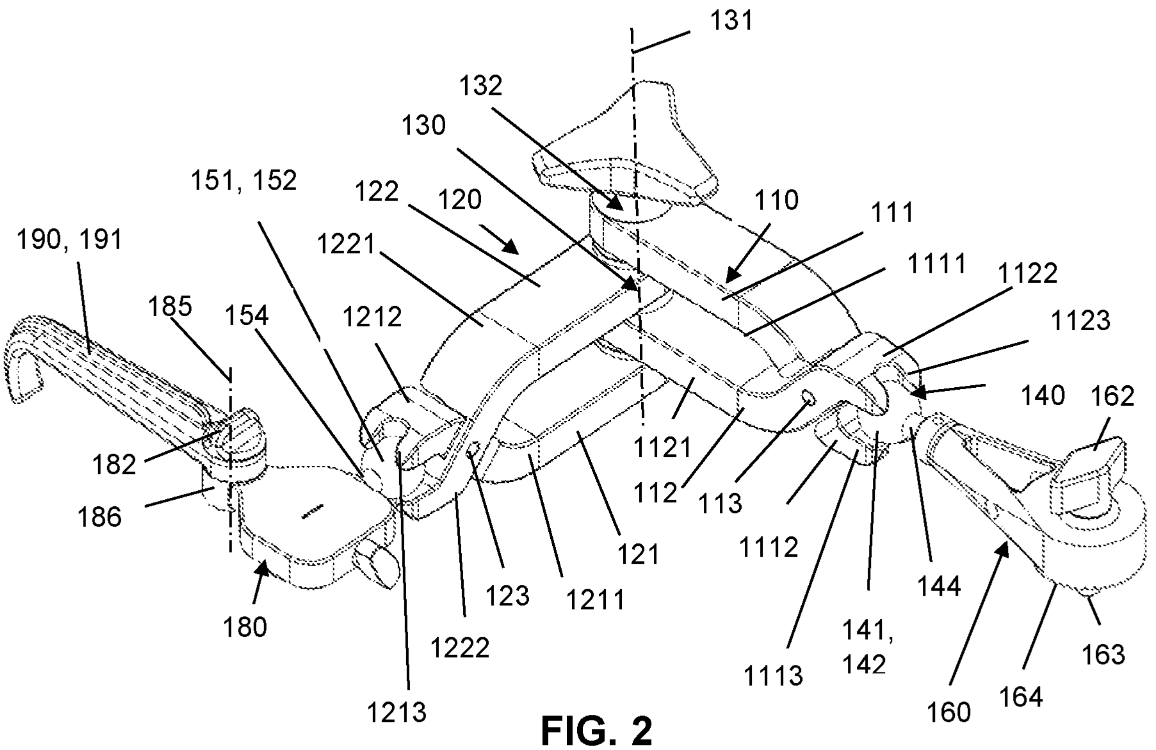
FIG. 2 depicts a variant of FIG. 1, in which the clamping bodies of the outer joints are formed by balls and an instrument in the form of a hook is arranged on one of the outer joints on a universal adapter.

As used throughout the present disclosure, unless specifically stated otherwise, the term "or" encompasses all possible combinations, except where infeasible. For example, the expression "A or B" shall mean A alone, B alone, or A and B together. If it is stated that a component includes "A, B, or C", then, unless specifically stated otherwise or infeasible, the component may include A, or B, or C, or A and B, or A and C, or B and C, or A and B and C. Expressions such as "at least one of" do not necessarily modify an entirety of the following list and do not necessarily modify each member of the list, such that "at least one of "A, B, and C" should be understood as including not only one of A, only one of B, only one of C, or any combination of A, B, and C.

Similar elements are generally indicated in the figures with the same or similar reference numerals.

A positioning arm 100 shown in FIG. 1 comprises a first arm element 110 and a second arm element 120, which are connected to each other by a central joint 130. At an end remote from the central joint 130, the first arm element 110 comprises a further joint 140 through which the positioning arm 100 is connectable to a fastening device 160.

At an end remote from the central joint 130, the second arm element 120 comprises a further joint 150 through which the positioning arm 100 is connectable to a universal adapter 170.

The first arm element 110 is formed by an outer pincer arm 111 and an inner pincer arm 112, which are connected to each other at a connecting joint 113 formed, for example, by a bolt 1131. The outer pincer arm 111 comprises a lever arm 1111 starting from the central joint 130 and a gripping arm 1112 between the connecting joint 113 and the further joint 140. The inner pincer arm 112 comprises a lever arm 1121 starting from the central joint 130 and a gripping arm 1122 behind the connecting joint 113 in the direction of the further joint 140.

At least one gripper 1113 is formed on the gripping arm 1112 and at least one gripper 1123 is formed on the gripping arm 1122. The inside of the gripping arm 1112 comprises a concave recess 1114 and the inside of the gripping arm 1122 comprises a concave recess 1124. The grippers 1113 of the gripping arm 1112 and the grippers 1123 of the gripping arm 1122 enclose a clamping body 141 of the further joint 140, which in FIG. 1 is in the form of a rotating sleeve 143. The rotating sleeve 143 is shown enlarged in FIG. 14. The rotating sleeve 143 comprises a ring groove 1431 at a distance from its rear end. The rotating sleeve is divided into four segments 1432 by four slits 1433 evenly distributed in the outer shell parallel to the axis. The slits 1433 extend beyond the ring groove 1431. The diameter of the front circular opening of the rotating sleeve 143 is such that a ball 142 is insertable into the interior of the rotating sleeve 143 by slightly expanding the segments 1432. The interior of the rotating sleeve 143 preferably comprises a bulbous shape adapted to the ball 142.

The ball 142 is connected to a cylindrical connecting piece 144, which preferably has an external thread formed thereon that is not shown and which can be screwed into a matching internal thread of the fastening device 160, which is also not shown.

The second arm element 120 is formed by an outer pincer arm 121 and an inner pincer arm 122, which are pivotably connected to one another in a connecting joint 123 formed, for example, by a bolt 1231. The outer pincer arm 121 comprises a lever arm 1211 starting from the central joint 130 and a gripping arm 1212 between the connecting joint 123 and the further joint 150. The inner pincer arm 122 comprises a lever arm 1222 starting from the central joint 130 and a gripping arm 1222 behind the connecting joint 123 in the direction of the further joint 150.

At least one gripper 1213 is formed on the gripping arm 1212 and at least one gripper 1223 is formed on the gripping arm 1222. The inside of the gripping arm 1212 comprises a concave recess 1214 and the inside of the gripping arm 1222 comprises a concave recess 1224. The grippers 1213 of the gripping arm 1212 and the grippers 1223 of the gripping arm 1222 enclose a clamping body 151 of the further joint 150, which in FIG. 1 is configured in the form of a rotating sleeve 153. The rotating sleeve 153 is shown enlarged in FIG. 14. The rotating sleeve 153 comprises a ring groove 1531 at a distance from its rear end. The rotating sleeve 153 is divided into four segments 1532 by four slits 1533 evenly distributed in the outer wall parallel to the axis. The slits 1533 extend beyond the ring groove 1531. The diameter of the front circular opening of the rotating sleeve 153 is such that a ball 152 is insertable into the interior of the rotating sleeve 153 by slightly expanding the segments 1532. The interior of the rotating sleeve 153 preferably comprises a bulbous shape adapted to the ball 152.

The ball 152 is connected to a cylindrical connecting piece 154, which preferably comprises a male thread (not shown) that can be screwed into a matching female thread of a carrier 171 of the universal adapter 170, which is also not shown.

Figure 9:
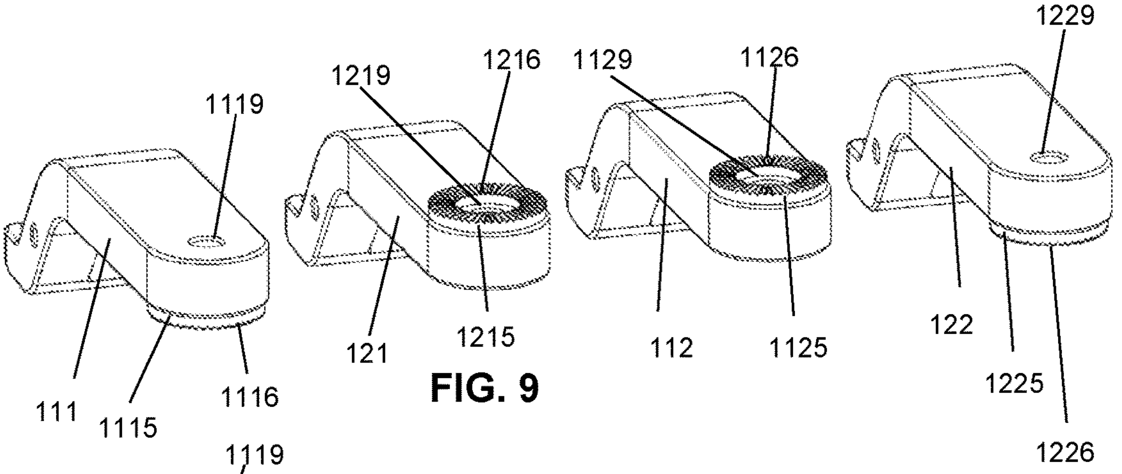
Figure 10:
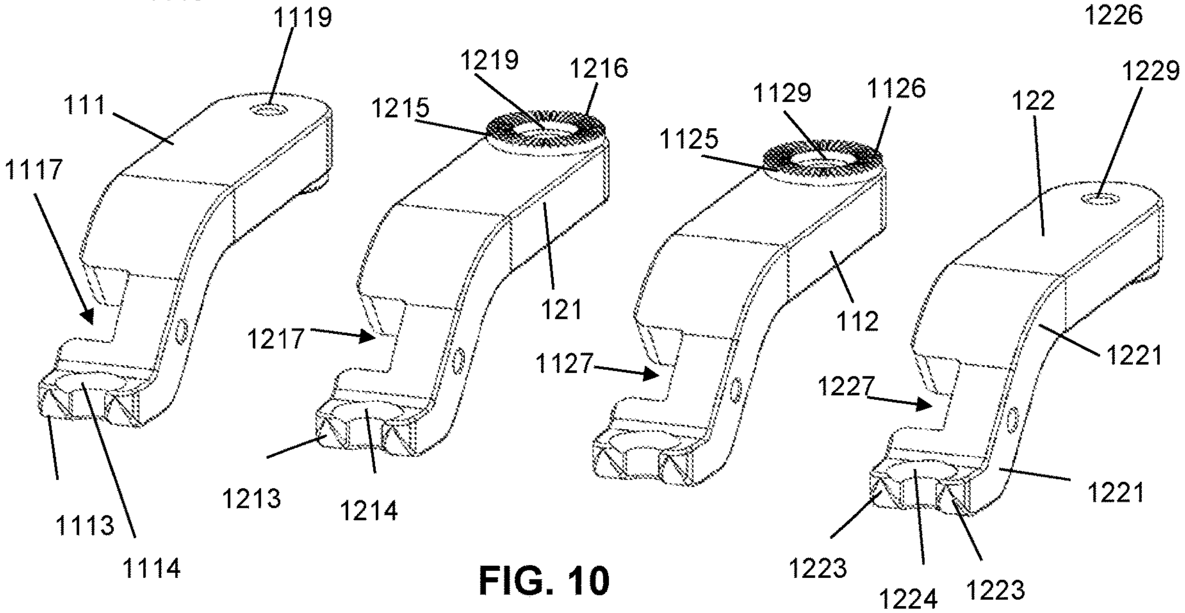
FIG. 10 depicts the pincer arms shown in FIG. 9 side by side in a perspective view from the side of the other joints.
Figure 11:
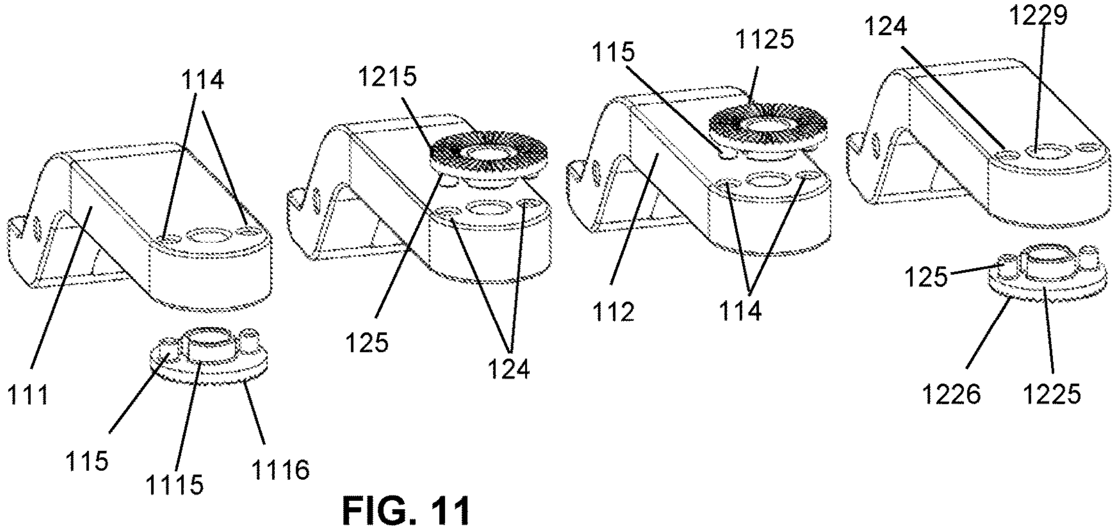
FIG. 11 depicts variant of the pincer arms shown in FIGS. 9 and 10, with separately formed latching elements that can be positively connected to the pincer arms.
Figure 12:
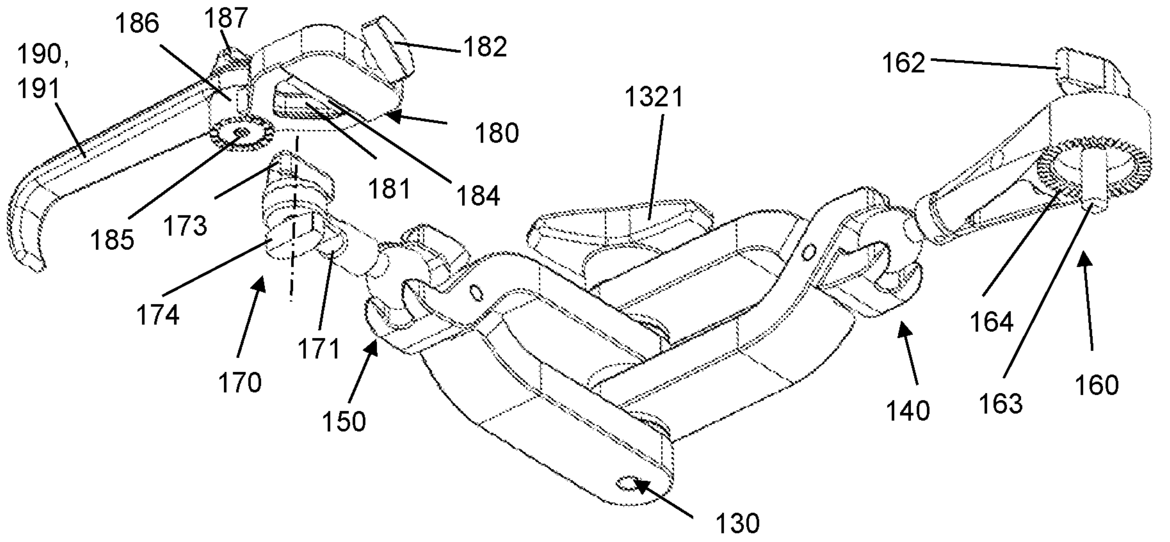
FIG. 12 depicts the variant shown in FIG. 2 in a perspective view from below with the holder for the hook-shaped tool removed from the universal adapter.
Figure 13:
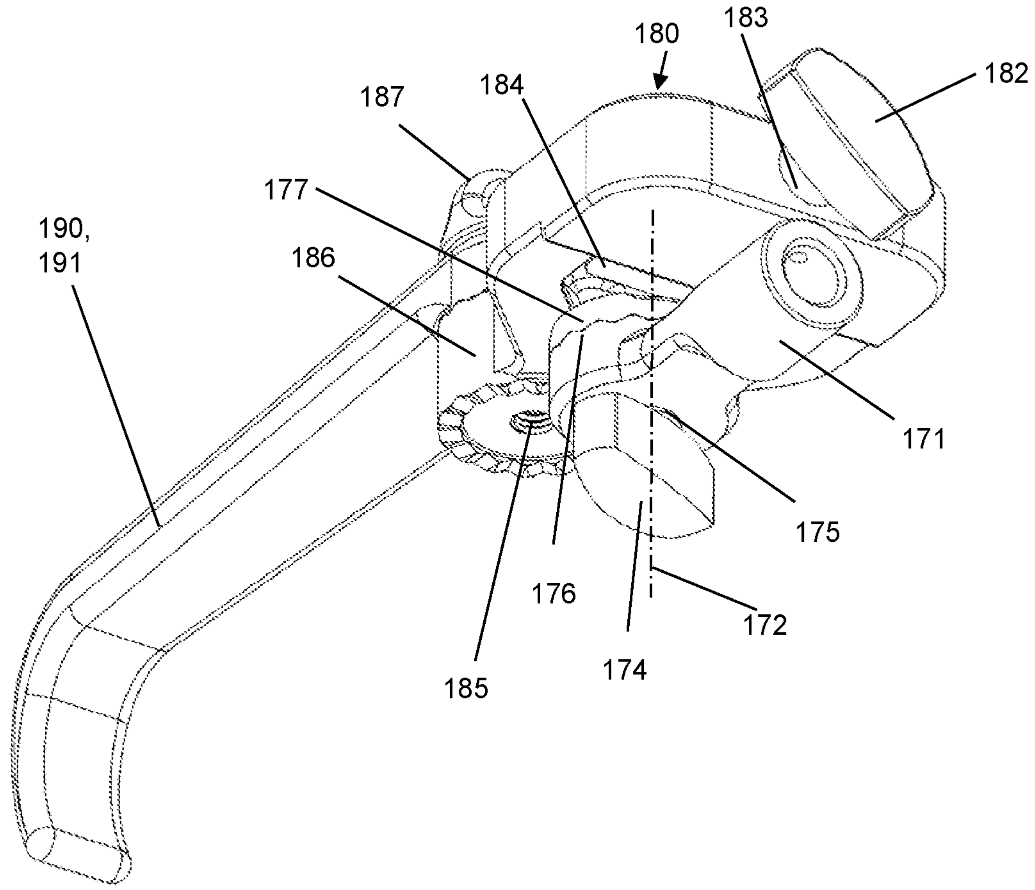
FIG. 13 depicts Enlarged view of the connection between the universal adapter and the holder shown in FIG. 12.

FIGS. 9 to 11 show the four pincer arms 111, 112, 121 and 122 as individual parts. It can be seen from the illustrations that the four pincer arms 111, 112, 121 and 122 can be manufactured as identical parts to the greatest possible extent, which greatly simplifies manufacture and stock-keeping. Furthermore, it can be seen from these figures that the pincer arm 111 comprises a bore 1119 formed as a through bore at its end facing the central joint 130. Similarly, the pincer arm 112 comprises a bore 1129, the pincer arm 121 comprises a bore 1219, and the pincer arm 122 comprises a bore 1229.

At least two of the pincer arms 111, 112, 121 and 122 comprise latching elements 1115, 1125, 1215 and 1225. In FIGS. 9 and 10, latching elements 1115, 1125, 1215 and 1225 are formed directly on pincer arms 111, 112, 121 and 122. The latching elements 1115, 1125, 1215 and 1225 comprise toothing 1116, 1126, 1216 and 1226, respectively.

In an alternative embodiment shown in FIG. 11, the latching elements 1115, 1125, 1215 and 1225, which are provided with toothing 1116, 1126, 1216 and 1226, are designed as independent disc-shaped components and each comprise two bolts 115 on the side opposite the toothing, which are configured to be positively engaged with corresponding locating holes 114 on the pincer arms 111, 112, 121 and 122.

The pincer arms 111, 112, 121 and 122 comprise an offset shape, with a transversely extending bore being provided approximately in the center of the offset for forming the connecting joints 113 and 123, respectively, by means of a through bolt. In these areas of the transversely extending bores, rectangular cutouts 1117, 1127, 1217 and 1227 are formed on the four pincer arms 111, 112, 121 and 122, which cutouts extend approximately to the center of the respective pincer arms and, in the assembled state, allow a respective pair of pincer arms 111 to engage with 112 and 121 with 122.

The pincer arms 111, 112, 121 and 122 can be manufactured inexpensively as identical parts in a robust design as an aluminum die casting or as a plastic injection molding.

The central joint 130 forms a pivot axis 131 for the first arm element 110 and the second arm element 120. The central or middle joint 130 connects—as best shown in FIG. 7—by means of a threaded rod 1322 through the bores 1119, 1129, 1219 and 1229 the rear ends of the first arm element 110 formed pincer-like by the outer pincer arm 111 and the inner pincer arm 112 and the rear ends of the second arm element 120 formed pincer-like by the outer pincer arm 121 and the inner pincer arm 122.

Figure 5:
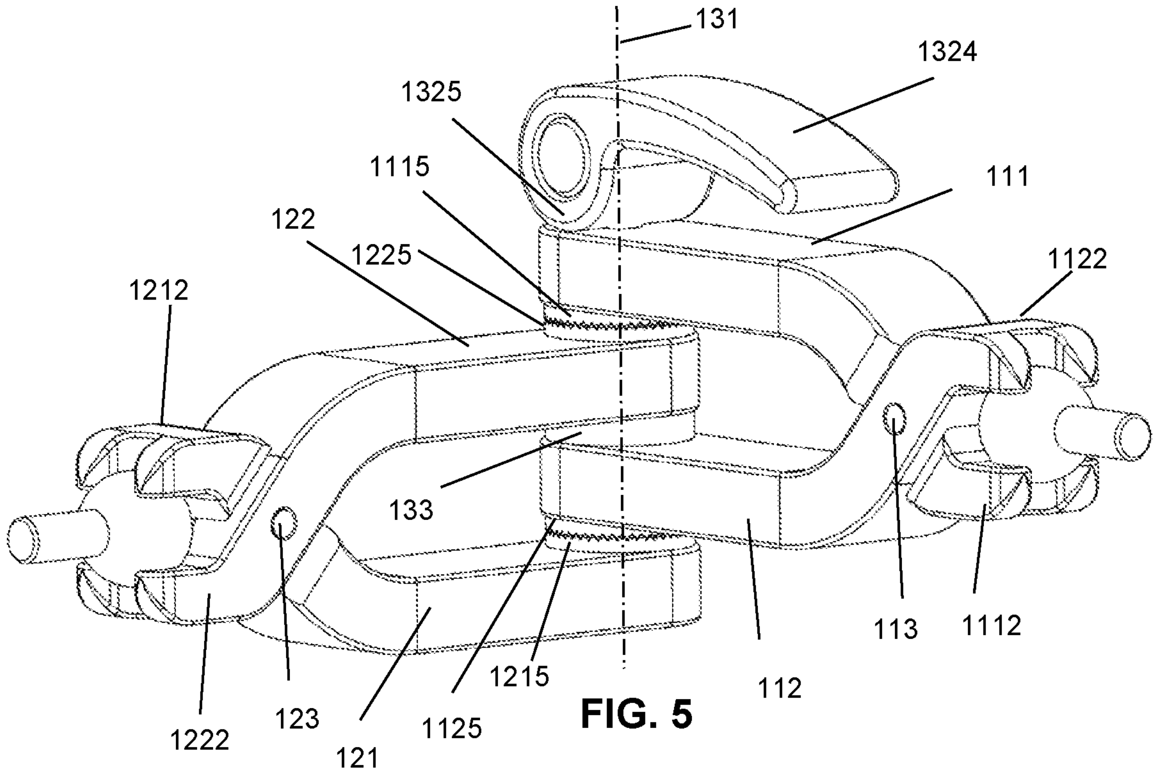
FIG. 5 depicts a variant of FIGS. 1 to 4 in which the blocking device of the central joint can be actuated by a clamping handle connected to an eccentric instead of a rotary handle.
Figure 6:
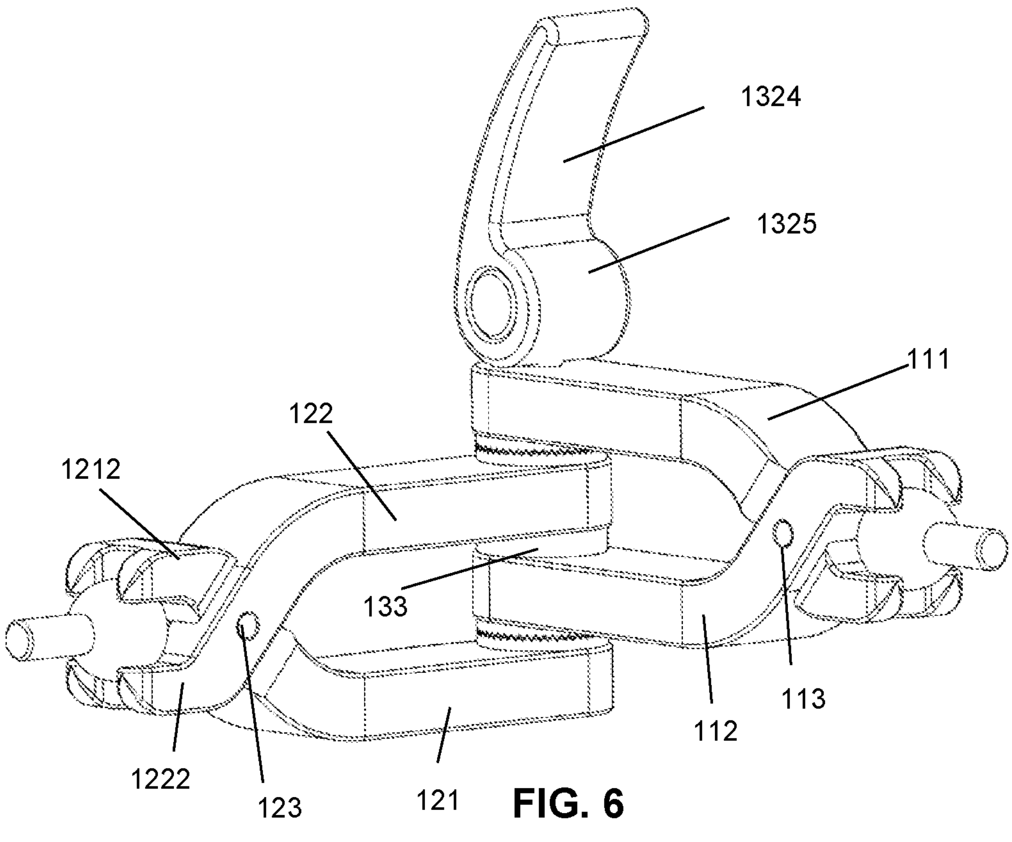
FIG. 6 depicts the variant shown in FIG. 5 with the clamping handle open.

In each case, the outer pincer arm 121 of the second arm element 120, the inner pincer arm 112 of the first arm element 110, the inner pincer arm 122 of the second arm element 120 and the outer pincer arm 111 of the first arm element 110 lie alternately one above the other from bottom to top. The threaded rod 1322 is connected at its upper end to an operating element formed as a rotary handle 1321 or, as shown in FIGS. 5, 6 and 8, as a clamping handle 1324 provided with an eccentric 1325.

Figure 7:
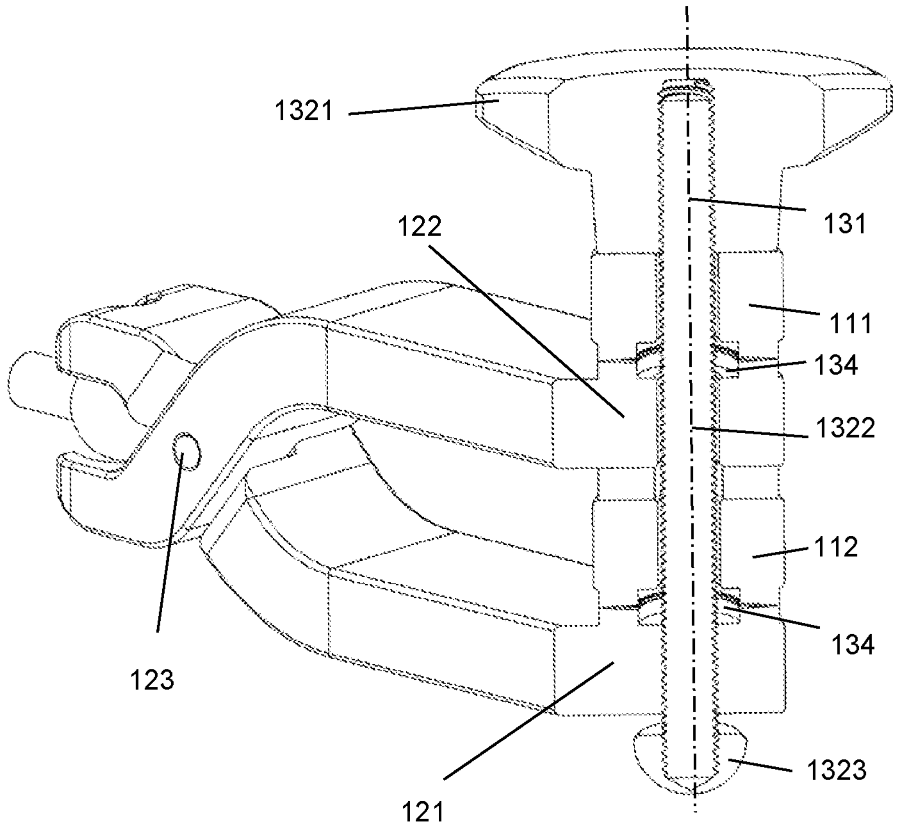
FIG. 7 depicts longitudinal section through the central joint with a rotary handle and two spring elements designed as disk springs.
Figure 8:
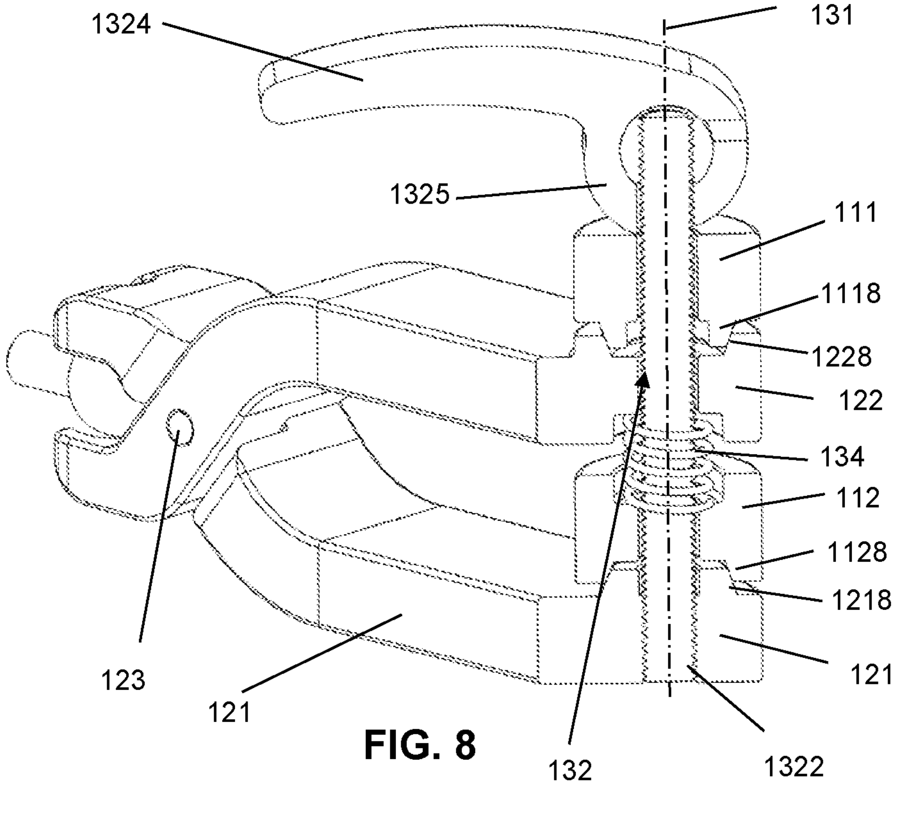
FIG. 8 depicts variant of FIG. 7 with a clamping handle and a centrally arranged spring element in the form of a coil spring, FIG. 9 the depicts four pincer arms forming the two arm elements side by side in a perspective view from the side of the central joint.

The lower end of the threaded rod 1322 is screwed either—as shown in FIG. 7—into a nut 1323 or—as shown in FIG. 8—directly into an internal thread of the outer pincer arm 121 formed in the area of the bore 1219.

Figure 20:
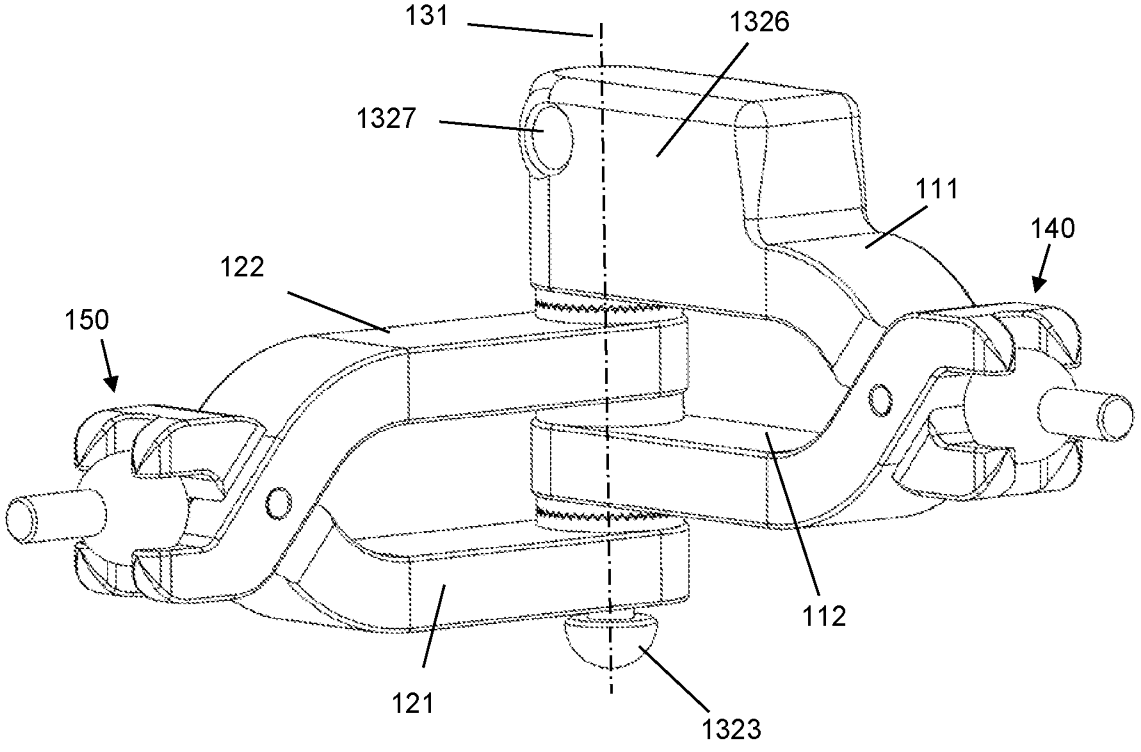
FIG. 20 depicts a variant of FIG. 4 with motor actuation of the locking device in the area of the central joint.
Figure 21:
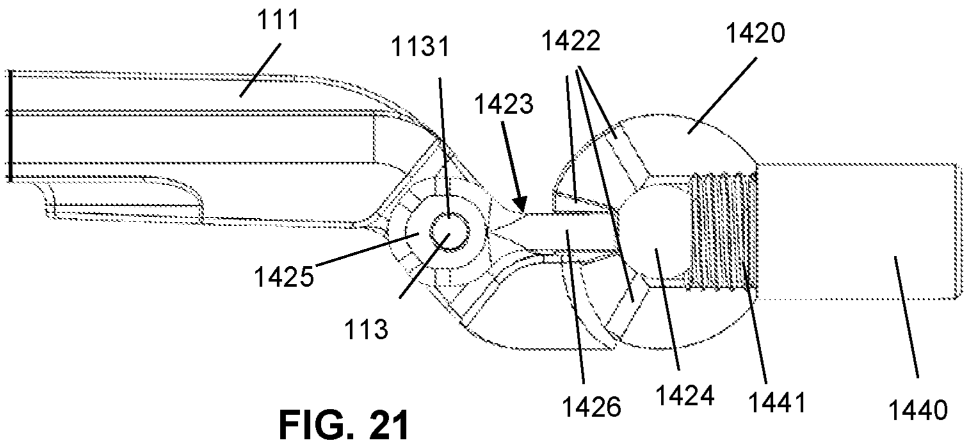
FIG. 21 depicts a variant with a tie rod mounted in a clamping body and attached to a connecting joint of the pincer arms, with one pincer arm omitted.
Figure 22:
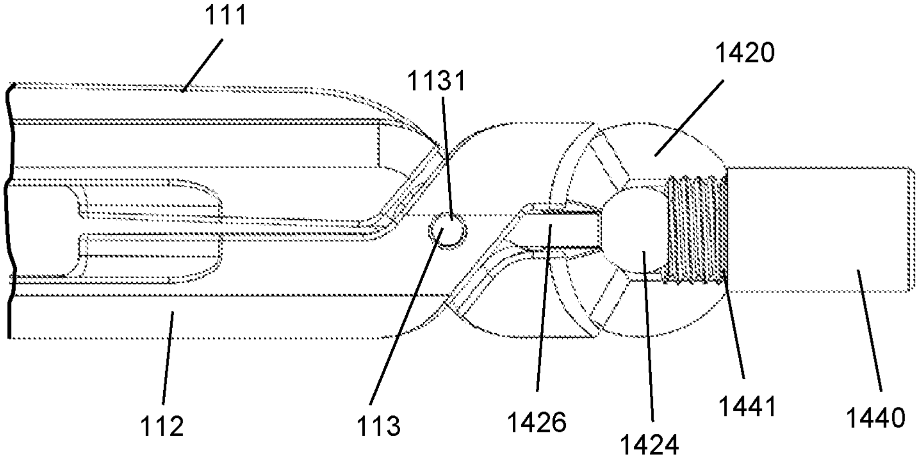
FIG. 22 depicts the variant according to FIG. 21 with both pincer arms.
Figure 23:
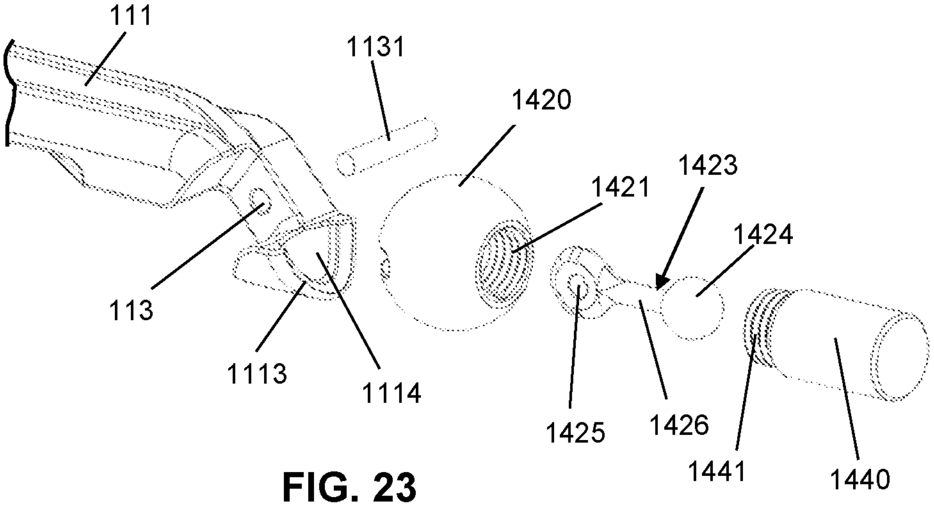
FIG. 23 depicts the variant according to FIG. 21 in exploded view in a first perspective.
Figure 24:
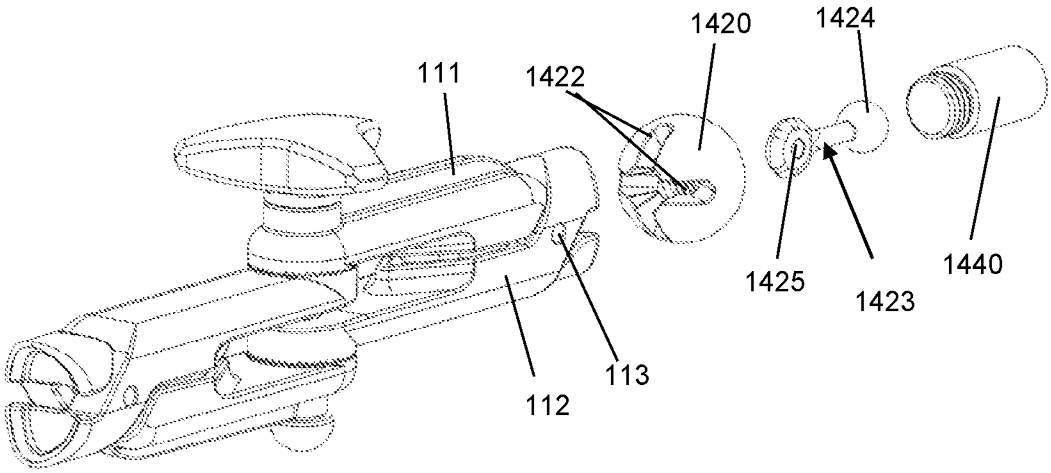
FIG. 24 depicts the variant according to FIG. 22 in exploded view in a second perspective.

The threaded rod 1322, in conjunction with the operating elements, namely the rotary handle 1321, the clamping handle 1324 or a motor 1326 indicated in FIG. 20, and the anchorage in the nut 1323 or the internal thread of the pincer arm 121, forms a blocking device 132.

The motor 1326 is preferably driven by an accumulator arranged in the housing, which is preferably integrally formed on the pincer arm 111, wherein the operating elements 1327 are arranged in an ergonomically favorable manner and the housing, as shown in FIG. 20, can also be used in an ergonomically favorable manner as a handle when guiding the positioning arm 100 into the desired position.

Tightening the operating elements 1321, 1324 or 1326 presses the ends of the pincer arms 111, 112, 121 and 122 against each other. In an only slightly tightened state, a swiveling movement about the pivot axis 131 is still possible. If, on the other hand, the operating elements 1321, 1324 or 1326 are tightened strongly, the swiveling movement of the arm elements 110 and 120 relative to each other is blocked in the central joint 130.

Figure 3:
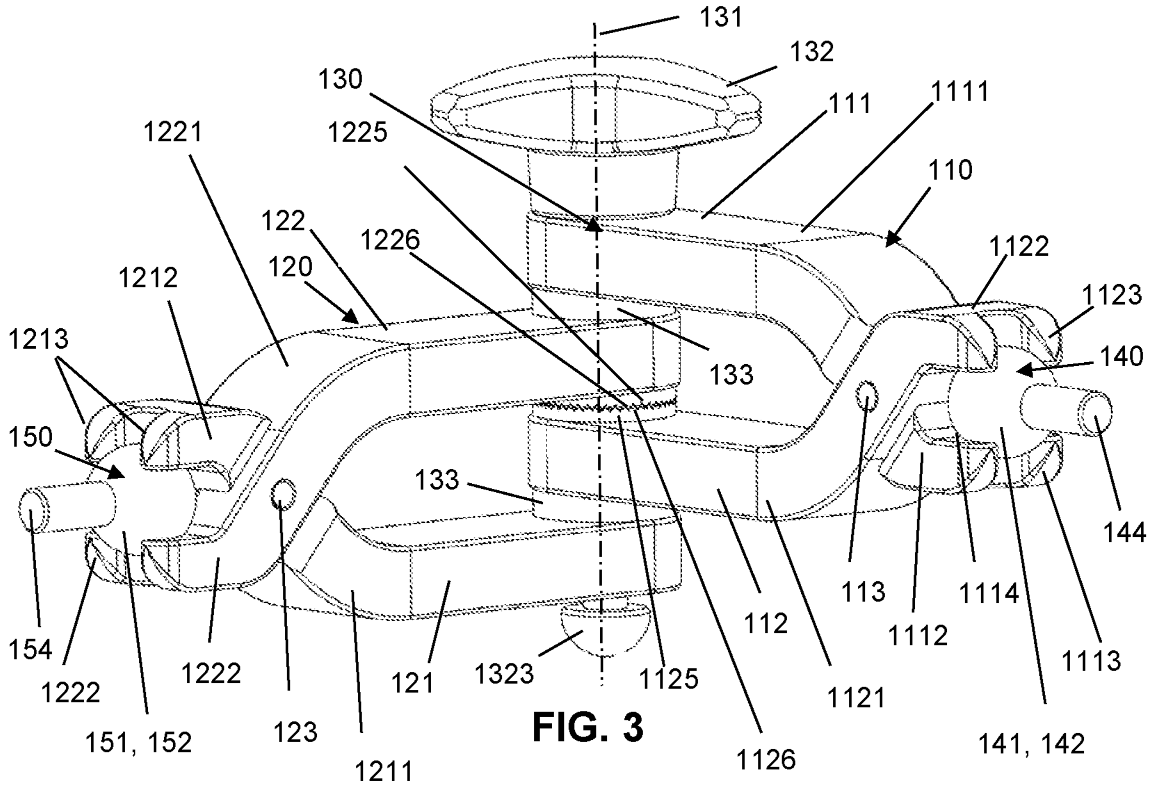
FIG. 3 depicts the variant shown in FIG. 2 with a central catch mechanism in the area of the central joint.
Figure 4:
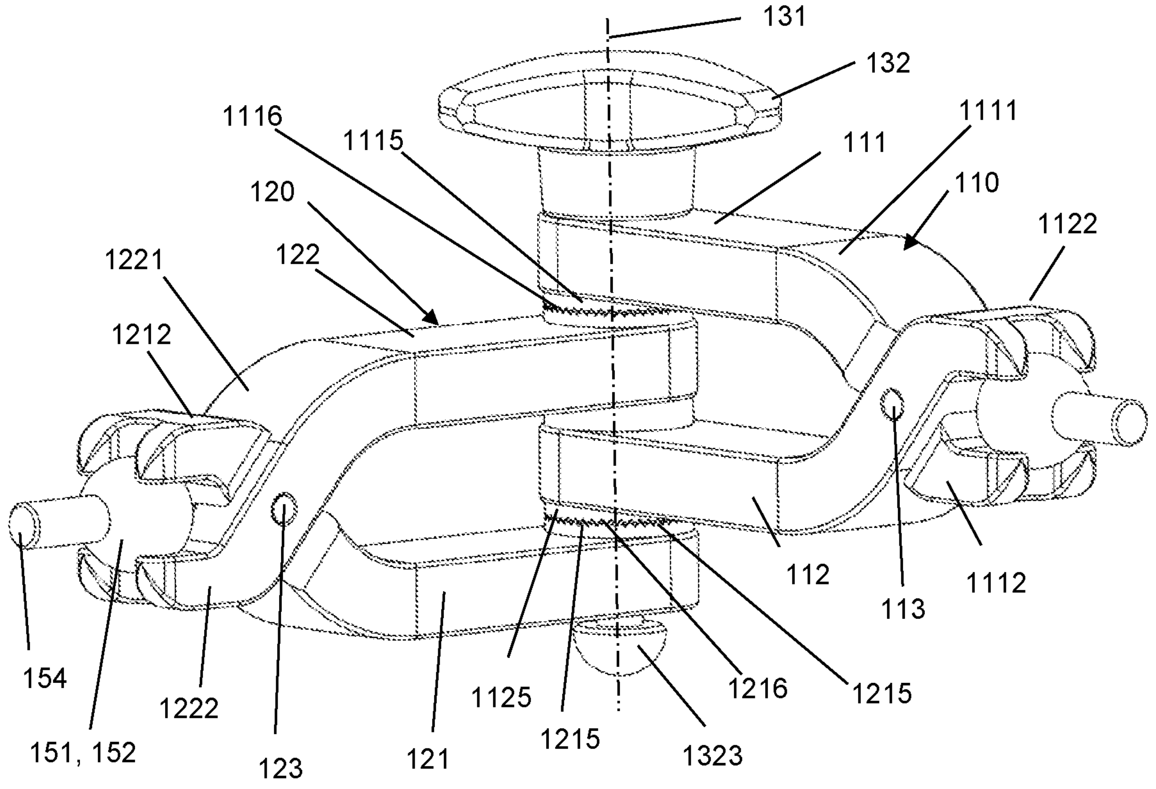
FIG. 4 depicts the variant shown in FIG. 2 with two decentralized catch mechanisms in the area of the central joint.

This locking can be reinforced by the interlocking toothing 1116, 1126, 1216 and 1226 of the latching elements 1115, 1125, 1215 and 1225. Two variants are possible here. As shown in FIG. 3, in a first variant a central engagement of the two latching elements 1126 and 1226 is possible. This embodiment is preferred when it is desirable to block the other joints 140 and 150 before blocking the center joint 130.

On the other hand, as shown in FIGS. 4, 5, 6 and 7, a second variant also allows decentralized engagement at two pairs of latching elements 1115 with 1225 and 1215 with 1125. In this case, an intermediate position of a spacer sleeve 133 is advantageous. This second variant is preferably used if locking of the central joint 130 is desired before locking of the other joints 140 and 150.

By blocking the middle joint 130 by means of the blocking device 132, the other joints 140 or 150 are also blocked simultaneously or with a slight time delay. When the pincer ends are pressed together at the lever arms 1111, 1121, 1211 and 1221 of the pincer arms 111, 112, 121 and 122, the gripping arms 1112 and 1122 of the first arm element 110 and the gripping arms 1212 and 1222 of the second arm element 120 are simultaneously pressed together. They thereby enclose the clamping bodies 141 and 151, respectively, which are formed either by balls 142 and 152, respectively, or by rotating sleeves 143 and 153, respectively, the rotating sleeves 143 and 153, respectively, in turn also being suitable for receiving balls 142 and 152, respectively, according to a particularly advantageous variant.

By means of different diameters of the balls 142 or 152 and/or by means of different thicknesses of spacer sleeves 133, it is possible to set very precisely which of the joints 130, 140 and or 150 locks first and which locks last when the blocking device 132 is actuated. According to an advantageous variant, for example, the joint 140 can block first after the positioning arm 100 has been roughly pivoted into the required position of use. When the blocking device 132 is further tightened, the central joint 130 can then block next, for example, and the further joint 150 last, after an instrument 190 arranged there on the universal adapter 170 has been rotated or pivoted into the target position. The sequence just described is only to be seen as an example. Any other sequence is also possible with a corresponding adjustment of the diameters or the diameters of the balls 142 or 152 and/or the rotating sleeves 143 or 153 and/or the thickness of the spacer washers 133. It is also possible to influence the timing of the locking of the respective joint 130, 140 or 150 by changing the length ratios of the lever arms to the gripping arms on the respective pair of pincer arms.

Instead of the latching elements 1115, 1125, 1215 and 1225, an outer cone 1118 on the pincer arm 111 engaging in an inner cone 1228 on the pincer arm 122 and an outer cone 1218 on the pincer arm 121 engaging in an inner cone 1128 on the pincer arm 112 can also assist the blocking device 132 in blocking the central joint 130, as shown in FIG. 8.

To ensure that the blocking device 132 of the central joint 130 opens easily when the rotary handle 1321, the clamping handle 1324 or the motor 1326 is opened, it is advantageous if at least one spring element 134 counteracts the closing force. In FIG. 8, a spiral compression spring surrounding the threaded rod 1322 is arranged in the central area of the threaded rod 1322 as an axial spring element 134 for this purpose. In FIG. 7, two spring elements 134 in the form of disk springs are arranged at an axial distance from one another between the pincer arms 111 and 122 and between the pincer arms 112 and 121, respectively, surrounding the threaded rod 1322.

Figure 19:
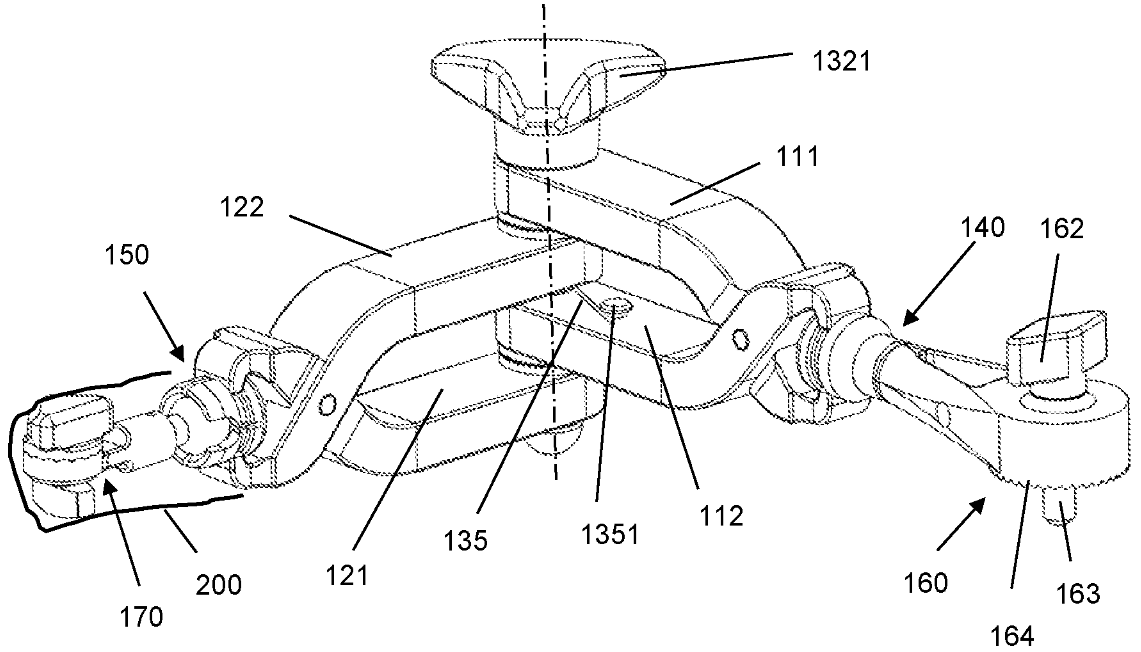
FIG. 19 depicts the variant according to FIG. 18 with completely shown pincer arms and a sterile sleeve or foil indicated in the area of the universal adapter.

Handling of the positioning arm 100 according to the invention is advantageously additionally facilitated by the fact that, as shown in FIGS. 18 and 19, a further spring element 135 is provided by means of which the first arm element 110 and the second arm element 120 are resiliently preloaded in a defined position relative to one another. Expediently, this is an extended position in which the first arm element 110 and the second arm element 120 enclose an angle of 180°. In the embodiment shown, the further spring element 135 is formed as a torsion leg spring which surrounds the threaded rod 1322 and whose ends are fixed to a stop 1351 on the pincer arm 112 or to a stop 1352 on the pincer arm 122.

As can be seen in FIG. 19, the fastening devices 160 are configured to be screwed into a holder, not shown, by means of a screw 163 connected to a rotary handle 162, which can be fastened, for example, to the side rails of an operating table. Locking toothing 164 is configured to also assist in securely fixing the positioning arm 100 in place.

At the other end on the patient side, a universal adapter 170 is particularly preferably provided adjacent to the second joint 150, which can be connected to the connecting piece 154, for example, by screwing it into a carrier 171. The universal adapter 170 comprises a shaped body 173, which is particularly preferably designed in the manner of a three-sided prism. The shaped body 173 is configured to be positively connected to a receptacle 181 on a holder 180, the shaped body 173 thereby being pressed in a wedge shape against the two inclined front flanks of the receptacle 181 when a slider 184, which is displaceably mounted on the holder 180, is pressed against it from behind by means of a rotary handle 182. The universal adapter 170 may additionally comprise a rotation axis 172 formed by a screw 175 with a rotary handle 174 arranged thereon (FIG. 19). Locking disks 176 on the carrier 171 and locking disks 177 on the shaped body 173 enable the shaped body 173 to be finely rotated and locked relative to the carrier 171, so that the holder 180 seated on the shaped body 173 can be correspondingly finely rotated and locked with the tools 190.

The prism of the shaped body 173 has no sharp corners and edges. If a sterile covering foil 200 (see FIG. 19) is placed between them, the foil 200 will not be damaged. This ensures that the sterile barrier formed by the covering foil 200 is not violated. At the same time, the prism of the shaped body 173 always allows a good and, above all, secure form fit (with and without the covering foil 200 in between), which ensures that the position of the instrument 190 attached to the universal adapter 170 is not changed.

As can be seen from FIGS. 15 to 17, the universal adapter 170 is configured to be used to connect a wide variety of tools and instruments 190 easily and quickly. In FIG. 15, the tool 190 is formed by a hook 191. In FIG. 16, a tool holder 186 is arranged on the holder 180, on which a needle guide 192 for guiding a needle 194 is mounted in the shown example. In FIG. 17, the holder 180 is equipped, by way of example, with a pair of tweezers 195 which can be fixed to the holder 180 by clamping. The holder 180 is preferably provided with a further rotation axis 185, so that the tool 190 can be rotated relative to the tool holder 186 and locked by means of a rotary handle 187.

The universal adapter 170 represents an independently inventive feature in its own right, as it is connectable by its shaped body 173 to any holders 180 for any tools 190, 191, 192, 193, 194 and 195. As a result, any tools 190, 191, 192, 193, 194 and 195 can be arbitrarily placed and quickly changed on a plurality of such positioning arms 100 as required during an operation. The positioning arm 100 according to the invention is also suitable for attaching preferably remotely operable robotic systems or patient positioning systems to the universal adapter 170. The locking of the joints 130, 140, 150 is so stable in the locked state that the entire operating table can be raised on the universal adapter 170 without the set position of the joints 130, 140, 150 changing in the slightest.

As can be seen from FIGS. 9 to 11, the positioning arm 100 according to the invention comprises very few pincer arms 111, 112, 121 and 122 which can be easily disassembled and assembled, so that disassembly for sterilization is possible in a simple manner.

Sterility can also be achieved in a simple manner by drawing a sterile covering foil 200 over the entire positioning arm 100. This is only indicated in FIG. 19 in the area of the further joint 150. The universal adapter 170 allows this cover 200 to be clamped non-destructively between the shaped body 173 and the receptacle 181 on the holder 180.

FIGS. 21 to 24 show another variant of a pincer arm. In this, the clamping body is formed by a partially hollow ball 1420, In a bore of the ball 1420, one end of which is provided with a thread 1421 and the other end of which is provided with slits 1422 arranged crosswise to each other, one end of a tie rod 1423 with a ball head 1424 is mounted. A shaft 1426 of the tie rod 1423 penetrates the slots 1422, and the tie rod 1423 is supported on the connecting joint 113 or a bolt 1131 forming the connecting joint by a bearing eye 1425 located at the other end of the tie rod 1423 and opposite the ball head 1424.

After the tie rod 1423 is inserted into the bore of the ball 1420, a connecting piece 1440 with its thread 1441 attached to one end is screwed into the thread 1421 of the ball 1420.

The ball 1420 is pulled by means of the tie rod 1423 when the pincer arms 111 and 112 are pressed together against a recess 1114, which is flatter in this case, of a gripper 1113 at the end of the pincer arms 111 and 112, thereby arresting a movement of the ball 1420. The teeth of the gripper 1113 are designed to be shorter in this variant than in the variants described first, in which the teeth of the grippers 1113, 1123, 1213, 1223 engage around the clamping bodies 141, 151 or the balls 142, 152 to more than half their diameter.

Figure 25:
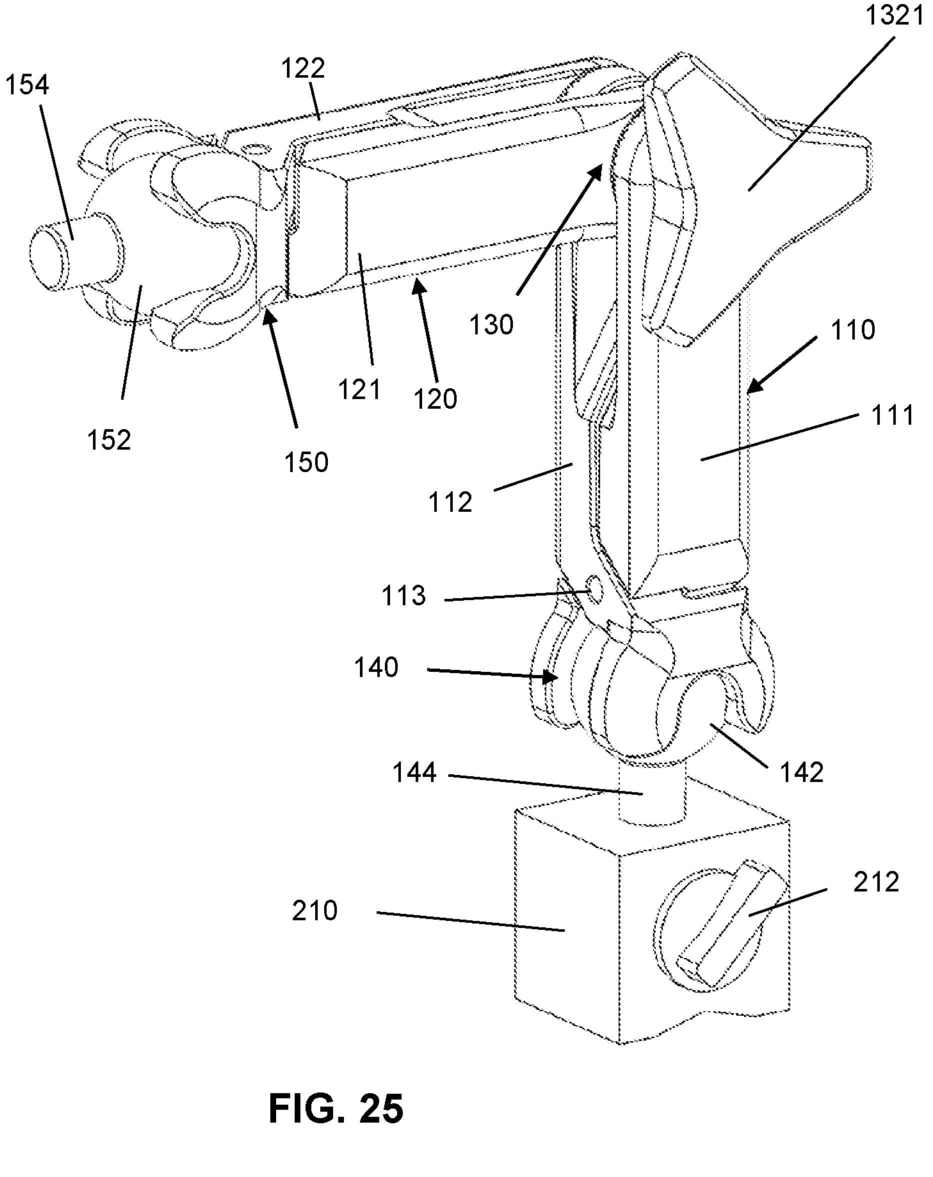
FIG. 25 depicts a positioning arm with a magnetic attachment located at the outer end of the first arm element.

FIG. 25 shows a further fastening option of a positioning arm according to the invention, in which a connecting piece 144 of a joint 140 is connected to a magnetic holder 210, which can be set to an active position or out of operation by means of a magnetic switch 212. By means of the magnetic holder 210, this positioning arm can be very easily fixed to metallic surfaces and released again.

Figure 26:
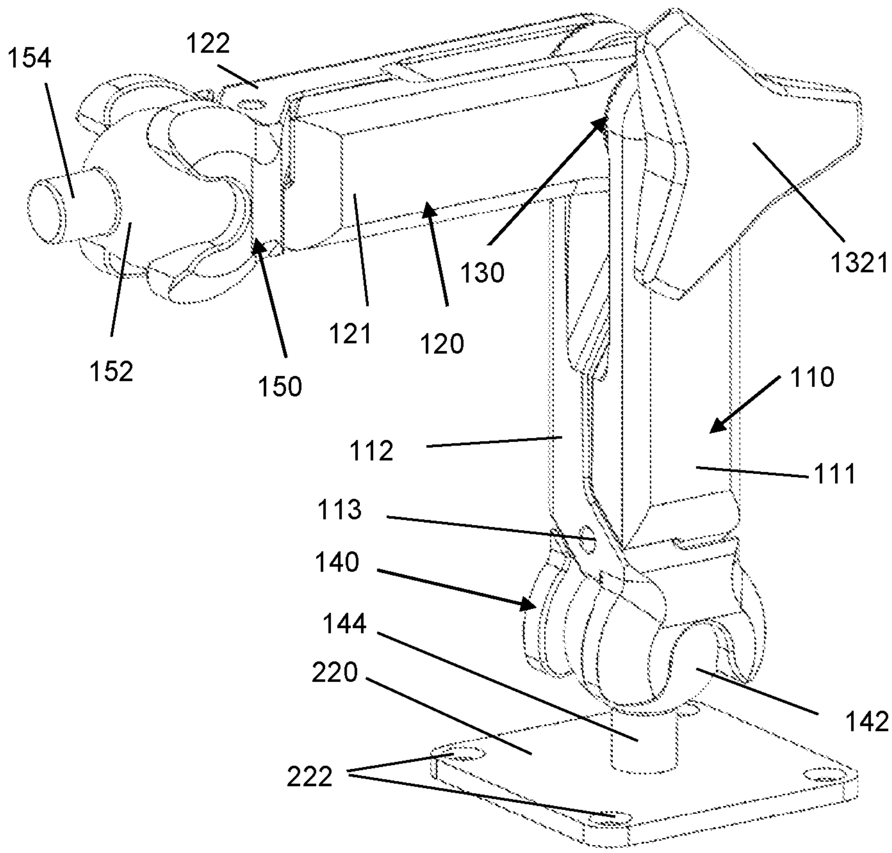
FIG. 26 depicts a positioning arm with a flange plate arranged at the outer end of the first arm element.

In FIG. 26, a connecting piece 144 of a joint 140 is connected to a flange plate 220 which comprises a plurality of bores 222 for attachment, for example by screws, to a carrier or to a wall.

Figure 27:
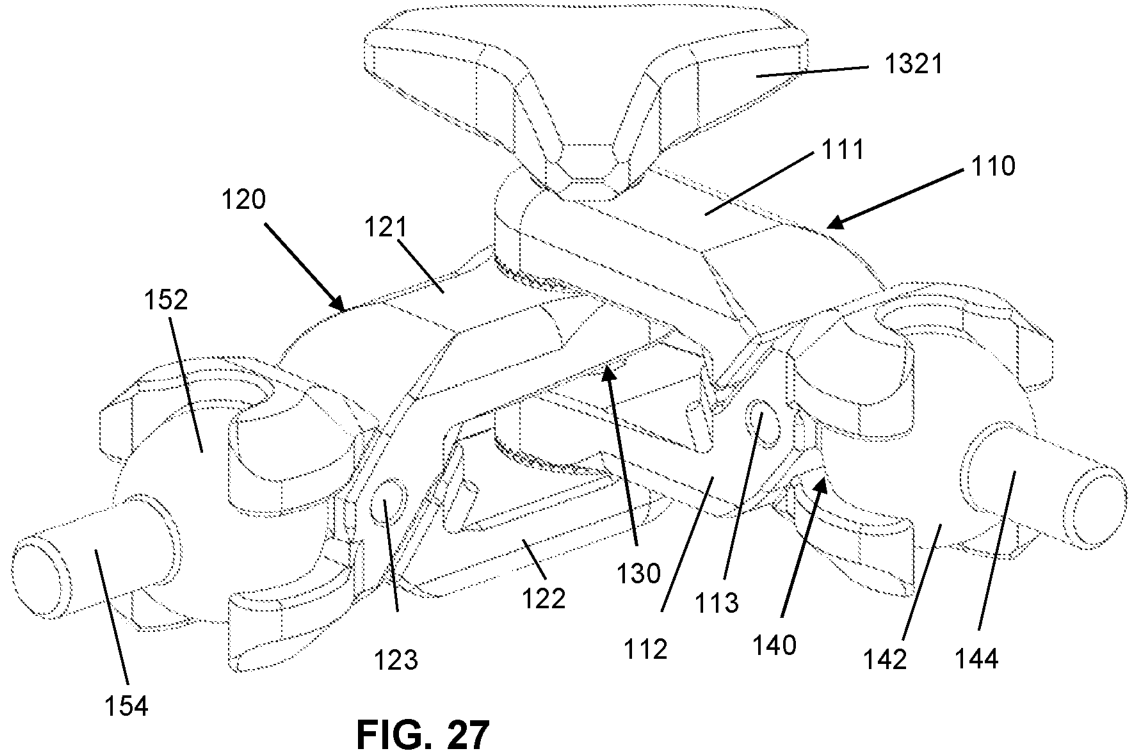
FIG. 27 depicts a variant with shortened pincer arms.

FIG. 27 shows a particularly small embodiment of a positioning arm in which the pincer arms 111, 112; 121 and 122 are very short and compact.

The scope of protection of the present invention is given by the claims and is not limited by the features illustrated in the description or shown in the figures.

The invention claimed is:

1. A positioning arm for positioning instruments, devices or tools, the positioning arm comprising:

at least a first arm element and a second arm element arranged pivotably connected to one another about a pivot axis by a central joint, wherein at least one of the at least first and second arm elements comprises a further joint arranged at an end opposite to the central joint, a blocking device configured to block and release the central joint and the further joint, wherein the blocking device is arranged at the central joint and is configured to effect the blocking and unblocking of the further joint via at least one transmission device formed at the first and second arm elements, wherein the transmission device is formed by a pair of outer and inner pincer arms which simultaneously also form one of the first and second arm elements, wherein the outer and inner pincer arms each comprise a lever arm and a gripping arm, wherein the lever arms are configured to be connected with rear ends thereof aligned in the region of the central joint by the blocking device such that the outer pincer arm of the second arm element, the inner pincer arm of the first arm element, the inner pincer arm of the second arm element and the outer pincer arm of the first arm element lie alternately one above the other, wherein the gripping arms form a part of the further joint, and wherein, when the rear ends of the lever arms are pressed together, the gripping arms are simultaneously pressed together.

2. The positioning arm according to claim 1, wherein:

each of the at least first and second arm elements comprise the further joint, and wherein the blocking device comprises a transmission device associated with one of the further joints.

3. The positioning arm according to claim 1, wherein the further joint comprises a rotatable clamping body.

4. The positioning arm according to claim 3, the rotatable clamping body comprises at least one of a ball and a rotating sleeve.

5. The positioning arm according to claim 1, wherein the blocking device comprises an actuating element configured to displace in an axial direction of the central joint and connect to an actuating device.

6. The positioning arm according to claim 5, wherein the actuating device-is comprises a rotary handle comprising a clamping handle connected to an eccentric or a motor.

7. The positioning arm according to claim 1, wherein one of the further joints comprises a fastening device configured to attach to an operating table, and another of the further joints is configured to connect to an adapter configured to attach to different instruments, devices or tools.

8. The positioning arm according to claim 1, wherein the pincer arms comprise identical parts.

9. The positioning arm according to claim 1, wherein the pincer arms comprise a light metal, a light metal alloy or a plastic material.

10. The positioning arm according to claim 1, wherein the blocking device comprises latching elements arranged or formed on the at least one transmission device.

11. The positioning arm according to claim 7, wherein the adapter comprises at least one shaped body configured to cooperate with a complementarily shaped receptacle of a holder of the tool, device or instrument.

12. The positioning arm according to claim 11, wherein the shaped body is configured to be fixed in the receptacle by means of a slider arranged on the holder.

13. The positioning arm according to claim 1, wherein the blocking device is configured and arranged to time-delay lock the central joint and the further-joints joint.

14. The positioning arm according to claim 1, wherein at least one spring element configured and arranged to counteract a closing force of the blocking device is arranged in a region of the central joint.

15. The positioning arm according to claim 1, wherein at least one spring element configured and arranged to preload at least one of the first and second arm elements into a predetermined basic position is arranged in a region of the central joint.

16. The positioning arm according to claim 3, wherein the clamping body is arranged connected by means of a tie rod to a connecting joint connecting the inner and outer pincer arms.

17. A positioning arm for positioning instruments or tools, the positioning arm comprising:

at least first and second arm elements arranged pivotably connected to one another about a pivot axis by a central joint, wherein at least one of the first and second arm elements comprises a further joint arranged at an end opposite to the central joint, a blocking device configured to block and release the central joint and the further joint, wherein the blocking device is arranged at the central joint and is configured to effect blocking and unblocking of the further joint via at least one transmission device formed at the first and second arm elements, wherein the transmission device is formed by a pair of outer and inner pincer arms which simultaneously also form one of the first and second arm elements, wherein the outer and inner pincer arms each comprise a lever arm and a gripping arm, wherein the lever arms are configured to be connected with rear ends thereof aligned in the region of the central joint by the blocking device such that the outer pincer arm of the second arm element, the inner pincer arm of the first arm element, the inner pincer arm of the second arm element and the outer pincer arm of the first arm element lie alternately one above the other, wherein the gripping arms form a part of the further joints, wherein, when the rear ends of the lever arms are pressed together, the gripping arms are simultaneously pressed together, and wherein one of the further joint is configured to connect to a universal adapter suitable for fastening different tools.

18. The positioning arm according to claim 17, wherein the universal adapter comprises at least one shaped body configured to cooperate with a complementary shaped receptacle of a holder for a tool or instrument.

19. The positioning arm according to claim 18, wherein the at least one shaped body comprises a three-sided prism with rounded corners and edges, and wherein the shaped body and the receptable are configured to clamp non-destructively to a sterile foil at least partially surrounding the positioning arm or the tool.

20. A positioning arm for positioning instruments, devices or tools, the positioning arm comprising:

at least two arm elements arranged pivotably connected to one another about a pivot axis by a central joint, wherein at least one of the at least two arm elements comprises a further joint arranged at an end opposite to the central joint, a blocking device configured to block and release the central joint and the further joint, wherein the blocking device is arranged at the central joint and is configured to effect the blocking and unblocking of the further joint via at least one transmission device formed at the at least two arm elements, wherein the transmission device comprises a pair of pincer arms arranged to simultaneously also form one of the at least two arm elements, wherein the further joint comprises a rotatable clamping body, and wherein the clamping body is arranged connected by a tie rod to a connecting joint connecting two pincer arms.

* * * * *